(12) United States Patent
Seewald et al.

(10) Patent No.: US 9,597,253 B2
(45) Date of Patent: Mar. 21, 2017

(54) METHOD AND APPARATUS FOR THE TREATMENT OF AMBLYOPIA

(71) Applicant: Caterna Vision GmbH, Berlin (DE)

(72) Inventors: Sascha Seewald, Dresden (DE); Nicolaus Widera, Dresden (DE)

(73) Assignee: Caterna Vision GmbH, Berlin (DE)

( * ) Notice: Subject to any disclaimer, the term of this patent is extended or adjusted under 35 U.S.C. 154(b) by 0 days.

(21) Appl. No.: 14/663,539

(22) Filed: Mar. 20, 2015

(65) Prior Publication Data
US 2016/0271001 A1    Sep. 22, 2016

(51) Int. Cl.
| A61B 3/00 | (2006.01) |
| A61H 5/00 | (2006.01) |
| A61B 3/028 | (2006.01) |
| A61B 5/00 | (2006.01) |
| A61B 3/032 | (2006.01) |

(52) U.S. Cl.
CPC ............... *A61H 5/00* (2013.01); *A61B 3/028* (2013.01); *A61B 3/032* (2013.01); *A61B 5/4833* (2013.01)

(58) Field of Classification Search
USPC .................................................. 351/200–246
See application file for complete search history.

(56) References Cited

U.S. PATENT DOCUMENTS

| 6,033,073 A * | 3/2000 | Potapova | A61B 5/04842 351/211 |
| 7,033,026 B2 * | 4/2006 | Spector | A61B 5/4041 351/246 |
| 8,454,166 B2 * | 6/2013 | Fateh | A61H 5/00 351/246 |
| 2001/0050754 A1 * | 12/2001 | Hay | A61H 5/00 351/213 |
| 2003/0214630 A1 | 11/2003 | Winterbotham | |

(Continued)

FOREIGN PATENT DOCUMENTS

| EP | 2329761 A1 | 6/2011 |
| WO | 2007026368 | 3/2007 |

(Continued)

OTHER PUBLICATIONS

Kaempf et al., "Unterstützende Amblyopiebehandlung durch Computerspiele mit Hintergrundstimulation: Eine placebokontrollierte Studie," Klinische Monatsblätter für Augenheilkunde, 2001; 218: 243-250.

(Continued)

*Primary Examiner* — Mohammed Hasan
(74) *Attorney, Agent, or Firm* — 24IP Law Group; Timothy R DeWitt

(57) ABSTRACT

A method for the treatment of amblyopia comprising the steps of diagnosis and approval of a patient by a medical practitioner, providing access to an eye-training platform for the approved patient and instructions to the approved patient on using the eye-training platform, preparation of a therapy protocol by the medical practitioner, use of the eye-training platform according to the therapy protocol, recordal of patient results, intermediate examination of the patient and review of patient results, further use of the eye-training platform according to a modified therapy protocol, recordal of further user results, and examination of visual acuity and review of user results by the medical practitioner.

13 Claims, 2 Drawing Sheets

(56) References Cited

U.S. PATENT DOCUMENTS

2010/0283969 A1    11/2010   Cooperstock et al.

FOREIGN PATENT DOCUMENTS

| WO | 2008070683 A1 | 6/2008 |
| WO | 2014041545 A1 | 3/2014 |
| WO | 2014205515 A1 | 12/2014 |

OTHER PUBLICATIONS

Haase, W. et al., "Ein neuer Test (C-Test) zur quantitativen Pruefung der Trennschwiergkeiten ("crowding")—Ergebnisse bei Amblyopie und Ametripie," Klin. Mbl. Augenheild. 180 (1982) 210-215.

* cited by examiner

METHOD AND APPARATUS FOR THE TREATMENT OF AMBLYOPIA

CROSS-REFERENCE TO RELATED APPLICATIONS

None.

BACKGROUND OF THE INVENTION

Field of the Invention

The present invention relates to a method for the treatment of amblyopia.

Brief Description of the Related Art

Amblyopia, also known as "lazy eye", designates a reduced vision in an eye that has mostly not received adequate use during early childhood. Quite often amblyopia results from either a misalignment of a child's eyes, such as crossed eyes, or a difference in image quality between the two eyes, with one eye focusing better than the other one of the two eyes.

The visual acuity of one eye can becomes stronger under these circumstances, which leads to suppression of the image of the other eye. If this condition persists, the weaker eye with the suppressed image may loose more and more of its visual acuity.

With early diagnosis and treatment, the sight of the "lazy eye" may be restored avoiding surgical interventions. It is generally necessary to first treat or identify the underlying cause before treating the amblyopia.

Glasses are commonly prescribed to improve focusing or misalignment of the eyes. Surgery may be performed on the eye muscles to straighten the eyes, if non-surgical treatments are unsuccessful. The surgery may be helpful in the treatment of amblyopia by allowing the eyes to work together better.

Eye exercises are recommended either before or after surgery to correct faulty visual habits often associated with strabismus and to teach correct use of both eyes. Training of the lazy eye will usually be done by occlusion of the eye with the higher visual acuity.

International patent application No WO 2007/026368 (Rabner) teaches an apparatus for testing, diagnosing and treating vision or eyes of a patient. This patent application fails, however, to teach a method for treatment of amblyopia.

A publication by Kämpf et al, "Unterstützende Amblyopiebehandlung durch Computerspiele mit Hintergrundstimulation: eine placebokontrollierte Studie", Klinische Monatsblätter für Augenheilunkde, 2001; 2189: 243-250, shows the results of treating children for amblyopia using software games.

SUMMARY OF THE INVENTION

The present disclosure teaches a method for the treatment of amblyopia and an apparatus for performing the method.

The present disclosure provides a method for the treatment of amblyopia comprising the steps of diagnosis and approval of a patient by a medical practitioner and providing access to an eye-training platform for the approved patient and instructions to the approved patient on using the eye-training platform. The eye-training platform can be an on-line or off-line platform with the facility to record the use of the eye-training platform by the patient.

The medical practitioner prepares a therapy protocol by the medical practitioner. The therapy protocol is adapted to the individual patient to address the patient's needs. The eye-training platform is then used by the patient according to the therapy protocol and the patient results recorded for later analysis.

An intermediate examination of the patient and review of patient results is carried out and, if appropriate, a modified therapy protocol can be developed. The modified therapy protocol could be identical with the original therapy protocol if suitable and the further user results recorded. The final examination of visual acuity and review of user results is carried out by the ophthalmologist.

In one aspect of the method, a compliance control is carried out after between five and ten days from beginning of use of the eye-training platform to ensure that the patient is using the method.

A time period of between 21 and 35 days is selected between the compliance control and the intermediate examination of visual acuity, as this has been found to be a suitable period of time to identify the first effects of the use of the eye-training platform.

A time period of at least 35 days is selected between the intermediate examination and final examination of visual acuity. It is, of course, possible after the final examination to continue using the eye-training platform if the medical practitioner considers this to be advisable.

To train the use of one eye, the eye-training platform offers the possibility of occlusion of one of the eyes.

The eye-training platform enables playing of software games with a background including attention-capturing stimuli. The software games do not provide any therapeutical benefit, but the attention-capturing stimuli are developed to train the eyes. These attention-capturing stimuli include, but are not limited to a narrowband wave pattern.

The amblyopia is caused by a anomaly of at least one of refraction, anisometropia or strabismus or a combination thereof.

The method is implemented on a web-based platform for the treatment of amblyopia, comprising a selection of interactive media displayed on a narrowband wave pattern.

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

BRIEF DESCRIPTION OF THE DRAWINGS

For a more complete understanding of the present invention and the advantages thereof, reference is now made to the following description and the accompanying drawings, in which.

DETAILED DESCRIPTION OF THE INVENTION AND THE FIGURES

Figure 1:
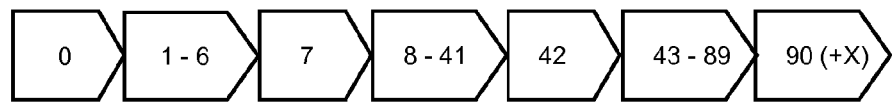
FIG. 1: Schematic illustration of a time bar indicating the sequence of method steps.
Figure 2:
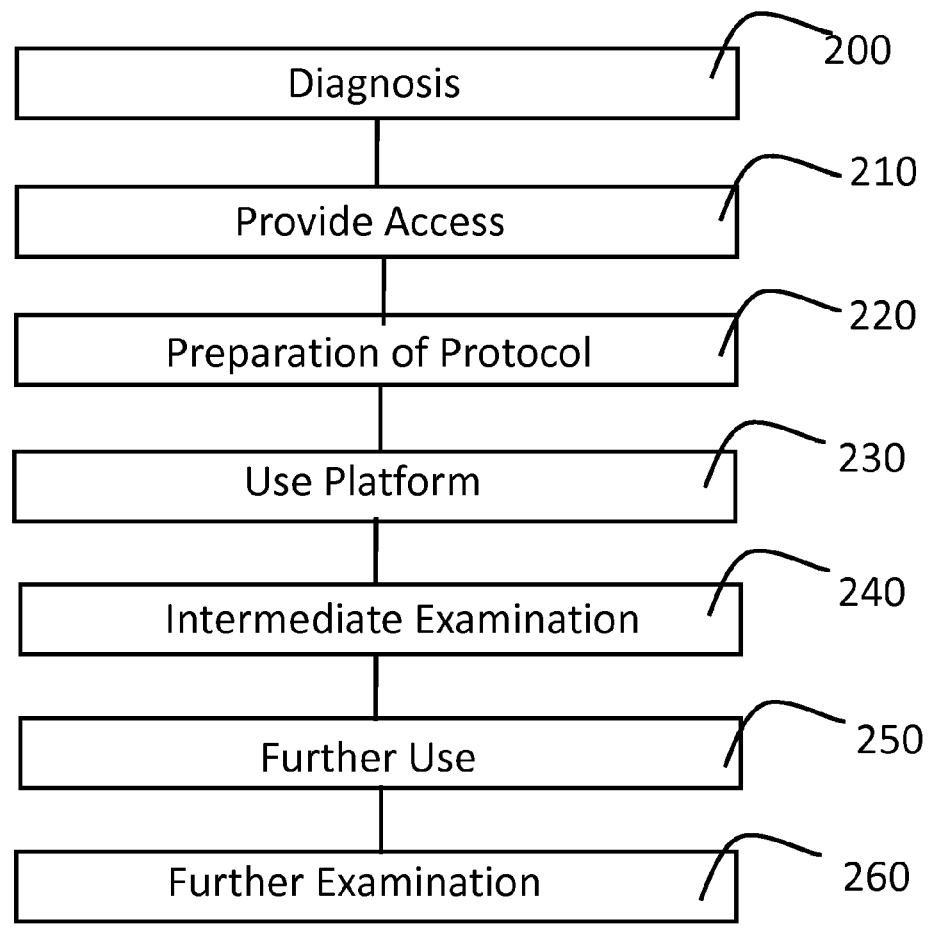
FIG. 2: An outline of a web-based apparatus for performance of the method.

The present disclosure provides a method for the treatment of amblyopia (shown in outline in FIG. 1) and an apparatus for performing the method (shown in FIG. 2). The method is particularly suitable for treating children between 4 years and 12 years, but can have wider application.

The term "treatment" in this document refers to an active treatment directed to the improvement of a defect, like amblyopia.

The term "mobile device" comprises, but is not limited to, mobile computer, cell phones, tablets, e-book reader or any other mobile device having an operating system and being suitable to run programs or applications.

The method of the present disclosure starts with evaluating a patient to determine whether he or she will benefit from a method using a web-based platform or other eye-training platform for eye training. This evaluation is usually carried out by an ophthalmologist, but could also be carried out by another doctor. A comprehensive anamnesis forms the basis for diagnosis and for approval that the patient will benefit from the eye-training platform.

The following criteria are, for example, determined for the anamnesis:
  Objective refraction in cycloplegia;
  Subjective refraction and visual acuity;
  Ophthalmologic fixation;
  Occlusion test; and
  Dot pattern test.

The results of the anamnesis are documented and values for settings in software for the eye-training platform are determined. The patient is instructed how to use the software and the eye-training platform.

The use of the eye-training platform is explained to the patient together with a protocol that the patient has to follow during the eye training. The protocol will include how often the patient should use the eye-training platform and will also include details of the games to be played. As noted above, the settings in the software have been determined and these settings can be programmed into the eye-training platform.

The daily use of the eye-training platform is recorded so that advantages or missing advantages can possibly related to the use of the eye-training platform. The eye-training platform records the time spent by the patient each day, which is recorded in a local database and can be electronically transmitted to the ophthalmologist or medical facility.

The use of the eye-training platform includes the playing of software games. Examples of such software games include, but a car racing game or a block-building game. These software games have no therapeutic function as such, but are used to keep the patients interested in using the eye-training platform. The therapeutic function is derived by superposing attention-capturing stimuli on top of the game. These attention-capturing stimuli capture the attention of the patient's eye and train the patient's eye. The attention-capturing stimuli include, but are not limited to, grids, wave-like forms or parallel lines moving over the screen of the eye-training platform and thus through the field of view of the patient. The frequency of the attention-capturing stimuli, their colour, distance apart, angle on the screen and colour can be adjusted to take into account the patient diagnosis. The values are entered into the software settings to control the eye-training platform.

A compliance control step is carried out after about seven days to ensure that the patient is using the correct therapy protocol.

An intermediate examination of the patient monitors changes in the visual acuity of the lazy eye being trained. In addition, the report of use is checked to ensure that the patient is using the software or the web-based platform correctly and sufficiently. If necessary, the therapy protocol can be adjusted and any necessary changes can be explained to the patient. This intermediate examination takes place around four to six weeks after commencement of the therapy and will check the acuity and fixation (using, for example, the C-Text of Haase, W. & Hohmann, A. (1982). Ein neuer Test (C-Test) zur quantitativen Prüfung der Trennschwierigkeiten ("crowding"). Ergebnisse bei Amblyopie and Ametropie. Klinische Monatsblätter der Augenheilkunde, 180, 210-215.Hohmann, A.

After 90 days or 12 weeks, a final examination of the patient takes place. The reports of the patient's therapy will checked. The results will be documented and possibly an extension of the therapy will be recommended.

It is intended that the therapy shall take place during occlusion of one of the eyes, i.e. the stronger eye, to strengthen the other one of the eyes. Thus, the overall time of eye training may be shortened.

An outline of the method is shown in FIG. 2. In step 200 a patient is examined by the medical practitioner and, using the results of the anamnesis discussed above, the medical practitioner decides whether the patient is suitable for therapy using the eye-training platform of this disclosure. Access to the eye-training platform is provided in step 210. The eye-training platform can be used in either on-line mode or an off-line mode.

The medical practitioner prepares the therapy protocol in step 220 and the patient then starts to use the eye-training platform in step 230 according to the therapy protocol developed by the medical practitioner.

An intermediate examination is carried out in step 240 between 26 and 45 days after the start of the use of the platform in step 230. It is possible to add a compliance control step after about 5 to 10 days from start of the use of the eye-training platform.

The medical practitioner can devise a modified therapy protocol after the intermediate examination has been carried out in step 240. This modified therapy protocol could be identical with the initial therapy protocol. The patient uses the eye-training platform further in step 250 and the results continue to be recorded. A further examination is carried out in step 260. This further examination 260 may be a final examination or the medical practitioner may suggest that the patient continue to use the eye-training platform to provide a further therapeutic benefit.

Figure 3:
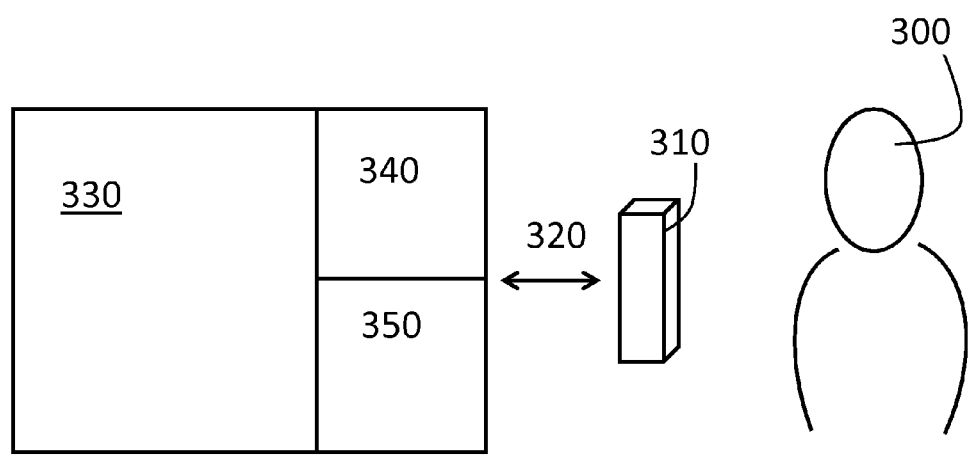
FIG. 3: An apparatus for the implementation of the method.

FIG. 3 shows an overview of the eye-training platform 330 as used by the patient 300. The patient 300 plays the computer game using peripheral devices, such as a screen 310 and joy sticks or keyboards (not shown). It will be appreciated that the peripheral devices and screen could be a tablet or a PC and can operated in on-line mode or off-line mode. The screen 310 is connected by a connection 320, which may be a Wi-Fi connection or a fixed line connection through the internet, to the eye-training platform 330. The eye-training platform 330 has a games module 340, which is used to generate the software games for playing by the patient. The eye-training platform 330 has in addition a training module 350, which is pre-programmed with the settings from the initial diagnosis in step 200. The training module 350 creates the attention-capturing stimuli, which are superposed onto the computer game from the games module 340 on the screen 310.

In an off-line mode, part of the games module 40 and the training module 350 will be run on the peripheral device, such as the tablet or the PC.

The therapy of the disclosure is well suited for children aged, for example, between four and twelve, because they are able train their lazy eye whilst playing software games. By adjusting concept, design, control and degree of difficulty of the software games, it is possible to individualize the use of the web based platform to the particular needs of the patient.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for the treatment of amblyopia comprising the steps of:
   a. Diagnosis and approval of a patient by a medical practitioner;
   b. Providing access to an eye-training platform for the approved patient and instructions to the approved patient on using the eye-training platform, the eye-training platform comprising a stimulation therapy for eyes and wherein the stimulation therapy comprises playing software games and superimposing attention-capturing stimuli on top of the software games;
   c. Preparation of a therapy protocol by the medical practitioner;
   d. Use of the eye-training platform according to the therapy protocol;
   e. Recordal of patient results;
   f. Intermediate examination of the patient and review of patient results
   g. Further use of the eye-training platform according to a modified therapy protocol;
   h. Recordal of user results; and
   i. Examination of visual acuity and review of user results by the medical practitioner.

2. The method of claim 1, further comprising a compliance control after between five and ten days from beginning of use of the eye-training platform.

3. The method of claim 1, wherein a time period of between 21 and 35 days is selected between the compliance control and the intermediate examination of visual acuity.

4. The method of claim 1, wherein a time period of at least 35 days is selected between the intermediate examination and final examination of visual acuity.

5. The method of claim 1, wherein the use of the eye-training platform comprises occlusion of one eye.

6. The method of claim 1, wherein the eye training platform is provided online.

7. The method of claim 1, wherein the eye training platform is provided as an application for mobile devices.

8. The method of claim 1, wherein the superimposed attention-capturing stimuli comprise a narrowband wave pattern.

9. The method of claim 1, wherein the eye-training platform is used for a maximum of 1 hour per day.

10. The method of claim 1, wherein the user results comprises at least one of the following features: length of use of the eye-training platform, time of occlusion indicating which one of the eyes was occluded, and the selected games of the eye-training platform.

11. The method of claim 1, wherein children are selected as suitable patients.

12. The method of claim 11, wherein the age of the children is between 4 and 12.

13. The method of claim 1, wherein the amblyopia is caused by a anomaly of at least one of refraction, anisometropia or strabismus or a combination thereof.

* * * * *